United States Patent [19]

Elliott et al.

[11] 4,051,049
[45] Sept. 27, 1977

[54] LUBRICATING OIL CONTAINING ALKANOIC AMIDE OR ESTER-BRIDGED HYDROCARBYL SUBSTITUTED PHENOLS

[75] Inventors: John Scotchford Elliott, Beaconsfield; Bryan Terence Davis; Richard Martin Howlett, both of Wokingham, all of England

[73] Assignee: Edwin Cooper and Company Limited, Bracknell, England

[21] Appl. No.: 666,912

[22] Filed: Mar. 15, 1976

Related U.S. Application Data

[62] Division of Ser. No. 462,092, April 18, 1974, Pat. No. 3,966,807.

[30] Foreign Application Priority Data

Apr. 19, 1973 United Kingdom .............. 19173/73

[51] Int. Cl.² .............................................. C10M 1/32
[52] U.S. Cl. ............................. 252/51.5 A; 252/47.5
[58] Field of Search .......................... 252/51.5 A, 47.5

[56] References Cited

U.S. PATENT DOCUMENTS

| | | | |
|---|---|---|---|
| 3,081,335 | 3/1963 | Morris et al. .................... | 252/47.5 X |
| 3,338,333 | 8/1967 | Spivack et al. ..................... | 252/47.5 |
| 3,462,368 | 8/1969 | Wollensak et al. .............. | 252/47.5 X |
| 3,590,083 | 6/1971 | Dexter et al. .................... | 252/47.5 X |
| 3,966,807 | 6/1976 | Elliot et al. ................ | 252/51.5 A X |

*Primary Examiner*—Delbert E. Gantz
*Assistant Examiner*—Andrew H. Metz
*Attorney, Agent, or Firm*—Donald L. Johnson; Robert A. Linn; Joseph D. Odenweller

[57] ABSTRACT

Bis-substituted phenols bridged through a carbon atom of an aliphatic carboxylic amide or ester are effective ashless dispersants for lubricating oil. Preferably, the phenols are substituted with a high molecular weight poly-alpha-olefin group.

10 Claims, No Drawings

LUBRICATING OIL CONTAINING ALKANOIC AMIDE OR ESTER-BRIDGED HYDROCARBYL SUBSTITUTED PHENOLS

PRIOR APPLICATION

This application is a division of application Ser. No. 462,092, filed Apr. 18, 1974 now U.S. Pat. No. 3,966,807.

BACKGROUND

This invention relates to compounds useful as lubricant additives.

Amongst the numerous types of additives used in blending lubricants, particularly but not exclusively automotive lubricants, are various surface active materials. For example, dispersants, particularly ashless dispersants, are incorporated in lubricants in order to disperse carbon particles and other insoluble materials such as decomposition products and fuel oxidation products in the oil medium which is the major constituent of the lubricants. The insoluble materials are thus suspended in the oil medium and prevented from forming deposits which can deleteriously affect engine operation.

Among the ashless dispersants proposed for the foregoing purpose have been certain derivatives prepared by reacting long chain alkyl phenols with aldehydes and polyalkylene polyamines to give Mannich bases. These compounds are excellent dispersants and impart some degree of oxidation resistance to lubricants in which they are incorporated, but in general they are deficient in thermal stability and also tend to derate the performance of the oils in diesel applications.

DESCRIPTION OF THE PREFERRED EMBODIMENTS

According to the present invention there is provided a compound having the general formula:

Formula 1

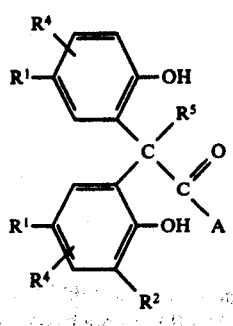

wherein $R^1$ is the same or different and is a hydrogen atom or an alkyl group, provided that at least one is an alkyl group containing at least 30 carbon atoms; $R^2$ is absent or is a group of the formula:

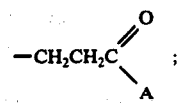

in which $m$ is zero or an integer; each $R^4$ is the same or different and is absent or a group of the formula — $Z-R^6$ in which $Z$ is a sulphur atom or a chain of two or more sulphur atoms or is absent and $R^6$ is an alkyl group or a hydroxy-substituted aralkyl group when $Z$ is absent or a hydroxy-substituted aryl or alkaryl group when $Z$ is present; each $R^5$ is the same or different and is a hydrogen atom, a methyl group or the group $$-CH_2CH_2C\underset{A}{\overset{O}{\diagup\!\!\!\diagdown}}\; ;$$

and each

is the same or different and is an amide or ester group provided that at least one is an amide group having at least one hydroxyalkyl or aminoalkyl substituent attached to the nitrogen atom.

At least one group $R^1$ in the compounds of the present invention is an alkyl group containing at least 30, preferably from 50 to 200, carbon atoms. Such alkyl groups may be derived from long chain olefins such as a poly-(alphaolefin), which may have molecular weights in the range of 700 to 3,000, more preferably 900 to 2000 and particularly about 1,000. Examples of suitable poly-(alphaolefins) are polyisobutylenes and polypropylenes.

The present invention also includes a process, wherein at least one bis (phenol substituted) carboxylic acid, or derivative thereof, having at least one alkyl substituent of at least 30 carbon atoms on a phenol substituent, is reacted with at least one aliphatic, cycloaliphatic or heterocyclic primary or secondary di- or polyamine or a hydroxy alkyl amine to form the corresponding amide.

The bis (phenol substituted) carboxylic acid starting material, or derivative thereof, employed in the process of the present invention is preferably a condensation product as described in our copending U.K. Application No. 50642/72. The products described in U.K. Application No. 50642/72 are condensation products of (i) an alkyl-substituted monohydric phenol, in which the alkyl substituent contains at least 8 carbon atoms, and (ii) a carbonyl-substituted compound selected from the group consisting of glyoxylic acid, pyruvic acid, levulinic acid, 3-oxoglutaric acid, 2-oxoglutaric acid and esters of such acids. Application No. 50642/72 also describes a compound having the general formula:

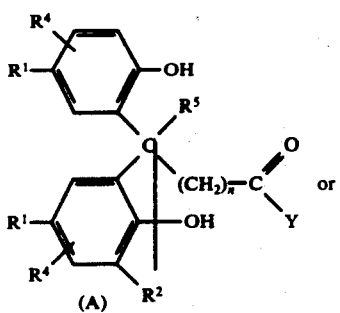

(A)

or

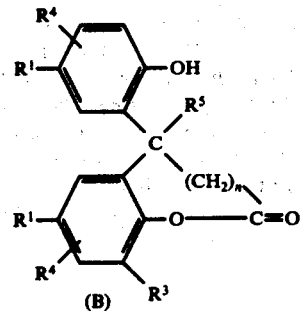

(B)

wherein each $R^1$ is the same or different and is an alkyl group containing at least 8 carbon atoms; $R^2$ is absent or is a group of the formula:

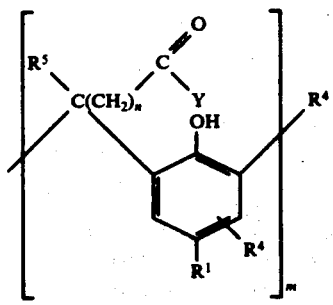

in which $m$ is zero or is an integer; $R^3$ is absent or is a group of the formula:

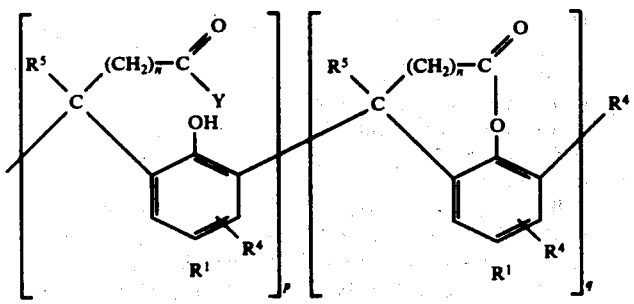

in which $p$ and $q$ are the same or different and are zero or are integers; each $R^4$ is the same or different and is absent or is a group of the formula $-Z-R^6$ in which Z is a sulphur atom or a chain of two or more sulphur atoms or is absent and $R^6$ is an alkyl group or a hydroxy substituted aryl, aralkyl or alkaryl group; each $R^5$ is the same or different and is a hydrogen atom, a methyl group or the group

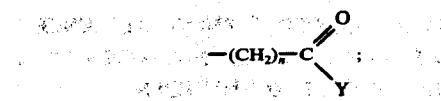

each $n$ is the same or different and is zero or an integer of from 1 to 2; and each Y is the same or different and is a hydroxyl group or an alkoxy group. It is to be understood that in the case where $R^3$ is a group of the formula (C), the groups

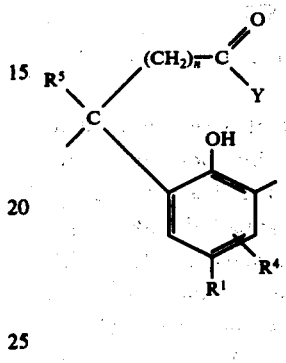

and

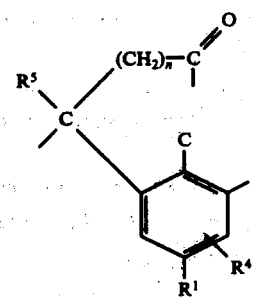

may be arranged in any order. For example, these groups may be randomly interspersed with each other and a block arrangement is not necessary.

In the case of the above-defined condensation products the alkyl substituted phenol starting material may bear one or more additional substituents on the aromatic ring and these correspond to the groups $R^4$ in the compounds of the foregoing formulae (A) and (B). When no (C)

substituent, other than the alkyl substituent, is present this corresponds to $R^4$ being a hydrogen atom. The alkyl substituent is preferably in the para-position corresponding to $R^1$ in formulae (A) and (B). Any other substituents are preferably positioned such that at least one ortho position is unsubstituted, so that the phenol may be condensed with the carbonyl compound at this position and thereby phenol residues are linked at the ortho-position as illustrated in formulae (A) and (B).

The groups $R^4$, or the substituents corresponding thereto in the case of the condensation products, may be absent or may be groups of the formula $-Z-R^6$ as hereinbefore defined. In a preferred embodiment $R^4$ is absent. That is to say the $R^4$ "substitutents", or corresponding "substituents" in the case of the condensation products, are hydrogen atoms. Such substances can be derived from alkylphenols having no substituent other than the alkyl substituent. In another embodiment the groups $R^4$, or corresponding substituents in the case of the condensation products, are present as groups of the formula $-Z-R^6$ in which Z is absent or is a sulphur atom or a chain of two or more, preferably 2 to 4, sulphur atoms. When Z is absent in this embodiment $R^6$ is an alkyl group, such as a short chain alkyl group containing 1 to 8, more preferably 1 to 4, carbon atoms or $R^6$ is a group of the formula:

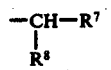

in which $R^7$ is a hydrogen atom or an alkyl group and $R^8$ is an aryl or alkaryl group containing at least one hydroxy substituent. Conversely, when Z is a sulphur atom or a chain of two or more sulphur atoms in this embodiment, $R^6$ is preferably an aryl or alkaryl group which bears a hydroxy substituent.

As starting materials in the process of the present invention may be used the foregoing novel substances of U.K. Application No. 50642/72, wherein at least one group $R^1$ in formulae (A) and (B) is an alkyl group of at least 30 carbon atoms, or the corresponding condensation product as detailed above, and wherein the group $R^5$ is a hydrogen atom, a methyl group or the group

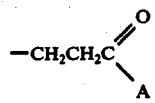

These starting materials are reacted with an amine, or mixture of amines, as hereinbefore defined. At least some of the amino groups present react with carboxylic groups to form amide groups and some, or all, of any hydroxyl groups present may, depending on the relative proportions of the reactants, form ester groups. However, it is preferred that all the groups

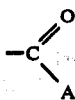

in the compounds of the present invention, or the corresponding groups of the products of the process of the present invention, are amide groups.

The amine starting material used to prepare the novel products of the present invention may be selected from a very wide range of amines. Preferred amines are alkylene polyamines having the general formula:

wherein $s$ is an integer and $R^9$ is a divalent alkylene radical. Preferably $R^9$ is an ethylene radical and $s$ is from 1 to 6, preferably 3 to 5. Examples of such amines are ethylene diamine, diethylene triamine, triethylene tetramine, tetraethylene pentamine, pentaethylene hexamine and mixed higher polyethylene polyamines. Other alkylene polyamines such as di(1,2-propylene) triamine, or N-(2-aminoethyl) trimethylene diamine may be employed, if desired. Such alkylene polyamines may be first reacted with a γ-lactone, preferably γ-butyro lactone as described in British Patent Specification No. 1,054,370 or with dicyandiamide as described in British Patent Specification No. 1,068,235.

Useful higher polyamines have molecular weights from 300 to 1000 or 5000, preferably 400 to 600, especially those prepared by polymerizing ethylene imine. The process of polymerising ethylene imine gives rise to mixtures of polyalkylene polyamines having a wide range of molecular weights. These may be divided into mixtures having narrow ranges of molecular weights, those indicated being the most useful in this invention.

Other polyamines which are useful in this invention are commercially available mixtures such as that predominantly consisting of a mixture of isomeric pentaethylene hexamines of formula $C_{10}H_{28}N_6$ and related hexamines containing piperazine rings and 12 C atoms. The average molecular weight of the mixture is approximately that of pentaethylene hexamine, i.e. 233, and the mixture contains a predominance of amines having 2 to 4 primary amino groups and at least two secondary amino groups.

Other suitable diamine compounds which may be employed are N-dialkylamino alkylamines of the general formula:

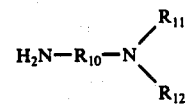

wherein $R_{10}$ is a divalent alkylene radical and $R_{11}$ and $R_{12}$ are alkyl radicals. Examples of such N - dialkylamino alkylamines include dimethylaminomethylamine, dimethylaminoethylamine, dimethylaminopropylamine, dimethylaminobutylamine, dimethylaminoheptylamine, diethylaminoethylamine, diethylaminopropylamine, diethylaminoamylamine, dipropylaminopropylamine, methylpropylaminoamylamine, and propylbutylaminoethylamine.

Further suitable diamino compounds are N - (β-aminoalkyl) piperazines of formula:

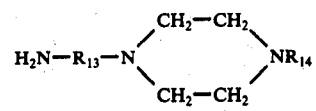

wherein $R_{13}$ is an alkylene radical containing 1 to 3 carbon atoms and $R_{14}$ is a hydrogen atom, a hydrocarbon radical containing from 1 to 3 carbon atoms or the group $-R_{13}-NH_2$.

Other miscellaneous di- or polyamine compounds which may be used in the invention are N - (2-aminoethyl)ethanolamine and hydroxyethyl triethylene tetramine.

The amine may be reacted with the bis(phenol substituted) carboxylic acid or derivative thereof in approximately equimolar proportions. In this embodiment, when using the preferred alkylene polyamine co-reactants or other amines initially containing two or more primary amino groups, the resulting reaction product will contain one or more residual primary amino groups. Alternatively, with the preferred linear alkylene polyamines, the amine may be reacted with up to twice the molar proportion of bis(phenol substituted) carboxylic acid or derivative thereof.

Alternatively, the amine and bis(phenol substituted) carboxylic acid or derivative thereof are reacted in equimolar proportions and one or more residual amino groups are reacted with a carboxylic acid, the form an amine salt, amide or imide thereof or imidazoline or condensed with aldehydes, ketones or mixtures thereof or with mixtures of aldehydes and phenols to form Mannich bases, in manner known per se. Alternatively, the amine may be first reacted with an appropriate molar proportion of a carboxylic acid, to provide an imide, amide or amine salt having a residual primary or secondary amino group, and the resulting imide, amide or amine salt reacted with the bis(phenol substituted) carboxylic acid or derivative thereof. In another embodiment of the present invention the amine is a polyamine in which one primary amino group is reacted, either before or after the amine has been reacted in equimolar proportions with the bis(phenol substituted) carboxylic acid or derivative thereof, with an alkyl substituted succinic acid or anhydride thereof containing from 8 to 200 carbon atoms in the alkyl substituent. Such substituents are preferably residues of comparatively low molecular weight polymers of olefins, such as isobutylene or propylene, or oligomers of such olefins.

The process of the present invention may be readily carried out by heating the co-reactants together and a preferred reaction temperature is from 50° to 250° C more preferably 130° to 220° C., most preferably from 180° to 220° C. An inert solvent, such as xylene, toluene or mineral oil may be used. The reaction may be most conveniently carried out in a vessel which is open to the atmosphere. However, if desired the reaction can be carried out under vacuum or low pressure conditions or under a nitrogen blanket. The reaction is usually completed within 1 to 6 hours, 2 to 4 hours being most common.

As hereinbefore described the bis(phenol substituted) carboxylic acids or derivatives thereof may be compounds as described in our U.K. Application No. 50642/72 and these compounds may contain more than one carboxylic group, either in free acid form or as, for example, an ester or lactone thereof. In addition the amine co-reactant may contain more than one amino group. Hence, the proportions of the co-reactants used may be selected according to the reaction product required. For example, stoichiometric molar proportions may be used so that all amino groups are reacted with all carboxylic groups present. Alternatively an excess of amine may be used so that the resulting reaction product will contain residual (unreacted) amine groups or when the bis(phenol substituted) carboxylic acid starting material is in the form of the ester derivative thereof an excess may be used so that the resulting reaction product will contain residual ester groups. However, in order to obtain optimum dispersancy at least two free amino groups should be present in the product for each molecule of amine reacted with a carboxylic acid group.

In yet another aspect of the present invention there is provided a lubricating composition containing a major amount of a lubricating oil and having dissolved therein a minor amount of an additive which is a compound or reaction product of the present invention or a mixture of such compounds and/or reaction products. Preferably, the lubricating compositions of the present invention contain from 0.3% to 15% by weight, preferably 1% to 6% by weight of the additive based on the total weight of the composition.

Also included within the scope of the present invention are additive concentrates comprising a minor amount of a lubricating oil and a major amount of one or more additives in accordance with the present invention, and additive packages comprising a minor amount of a lubricating oil and a major amount of a combination of one or more additives in accordance with the present invention and at least one other lubricant additive.

The lubricating oil used in the lubricating compositions of the present invention may be any of the well known synthetic ester oils, such as dioctyl sebacate. The preferred oils, however, are mineral oils of lubricating viscosity of well known type. It is especially preferred that the additive employed in the lubricating compositions of the present invention is a product prepared by reacting a polyisobutyl phenol, in which the polyisobutyl group has a molecular weight of from 900 to 2000, with glyoxylic acid and reacting the resulting intermediate with a polyethylene polyamine containing an average of from 4 to 6 amino groups, the molar ratio of the reactants being from 1.0 to 2.0 : 1 : 0.5 to 1.0.

The present invention will now be illustrated with reference to the following examples.

EXAMPLE 1 a. Preparation of PIB phenol-glyoxylic acid intermediate

A solution of polyisobutyl phenol prepared from 1000 mw polyisobutylene as described in Example 1 of our copending U.K. Application No. 50642/72 (0.7m., 692g.), glyoxylic acid monohydrate (0.7m., 64.4g.) and p-toluene sulphonic acid (5g) in toluene (500ml.) was heated at reflux temperature, under nitrogen, in a flask fitted with a Dean and Stark water separator until the evolution of water had ceased (34ml. of water were collected). The resulting solution was stripped of solvent to yield 750g. of red viscous liquid.

Acidity = 40mg. KOH/g.

Saponification value = 96mg. KOH/g.

b. Preparation of a di-amide

The product from part (a) (306.4g.) was mixed with 27. 9g. of tetra ethylene pentamine and heated at 200° C., under nitrogen, for 4 hours, after dilution with minerals oil (58g.), the product was filtered through filter aid.

Acidity = 6mg. KOH/g. (Calc. NIL)

Total base number = 52mg. KOH/g. (Calc. 60)

%N = 2.3 (Calc. 2.5)

EXAMPLE 2

Preparation of a diamide without isolation of the intermediate

A solution of polyisobutyl phenol (1.0m., 890g.), glyoxylic acid monohydrate (1.0m., 92g.) and p-toluene sulphonic acid (7g.) in toluene (600 ml.) was heated at reflux temperature, under nitrogen, in a flask fitted with a Dean and Stark water separator until the evolution of water had ceased (41ml. collected). The solution was allowed to cool a few degrees and then tetraethylene pentamine (0.5m., 94.5g.) was added. After distilling off the solvent the mixture was heated at 200° C., under nitrogen, for 4 hours. The product was filtered after dilution with mineral oil (181g., to give a theoretical 85% concentrate).

Acidity = 12mg. KOH/g. (Calc. NIL)
Total base number = 56mg. KOH/g. (Cal. 65)
%N = 2.4 (calc. 2.7)

EXAMPLES 3 to 11

Following the general method of Example 2 a number of amides were prepared without isolation of the intermediate. The general method was as follows:

Polyisobutyl phenol and glyoxylic acid monohydrate were dissolved in toluene or xylene, p-toluene sulphonic acid (0.1% based on the weight of the reaction solution) was added and the solution stirred and boiled under reflux, in an atmosphere of nitrogen until evolution of water, collected in a Dean and Stark apparatus, had virtually ceased. The solution was cooled to 80°-100° C and tetraethylene pentamine (TEPA) was added. The solvent was distilled out and reaction was continued for 4 hours at 200° C. The products were cooled, diluted with mineral oil and petroleum spirit (b.p. 62°/68° C.) and filtered through a pad of filter-aid. The petroleum spirit was removed by vacuum-stripping at up to 170° C. Yields were generally at least 90%. Residual acidities were low, the maximum being 7 mg. KOH/g.

Further details of these preparations are tabulated in the following Table 1. The thiobis PIB phenol starting material for Example 10 was prepared as follows:

Polybutyl phenol (ex 1000 m.w. PIB) (571.5g., 0.5 mole) was stirred, under nitrogen, at 195° C. in the presence of sulphur (16.0g., 0.5g. atom) and sodium hydroxide (4.0g.) Hydrogen sulphide was evolved, the rate of evolution being greatly reduced after 20 hours. The reaction was then stopped and the product was diluted with petroleum spirit (b.p. 62°/68° C.) The solution was washed with water/methanol (1:9) (2×250c.c.) and the solvent was removed by vacuum-stripping.

Yield: 563g., 97%; %S: 1.5: Calc:-1.4.

The methylene-bis-PIB phenol starting material of Example 11 was prepared as follows:

A mixture of polybutyl phenol (ex 1000 mw PIB) (102.6g., 0.1 mole), 40% formalin (4.1g., 0.05 mole), concentrated hydrochloric acid (1 c.c.) and toluene (60 c.c.) was stirred and boiled under reflux until 3.9 c.c. of water (Calc. 4.1 c.c.) had been collected in a Dean and Stark water separator. (4 Hours). The solution was vacuum-stripped at 130° C./20 mm and the product was filtered.

Yield: 82g.; Hydroxyl Value: 58.2mg. KOH/g. (Calc. 54.5).

EXAMPLES 12 to 17

A number of polymeric (mono-amides) of TEPA were prepared by the method described in Examples 3 to 11 (Table 1). These were then further reacted with other reactants to form succinimides, amides, Mannich bases and Schiff's bases. Details of these preparations are set out in the following Table 2.

Where alkenyl succinic anhydrides were used as the other reactant, these were added at the end of the amidation stage, and reaction was continued for 4 hours at 200° C., before the products were diluted and filtered.

For the preparations of the mixed amide/Mannich bases, the amides were cooled, rediluted with toluene, the alkyl phenols added and 40% aqueous formaldehyde (formalin) added dropwise at 90°-95° C. This temperature was maintained for 1 hour, and then the solution was heated to reflux, water being removed in a Dean and Stark apparatus. After addition of diluent oil, the products were filtered and vacuum-stripped.

For the preparation of the mixed amide/Schiff's base, the amide was diluted with xylene, the benzaldehyde was added, and the solution boiled under reflux, water being removed in a Dean and Stark apparatus. The product was diluted and filtered as before.

EXAMPLES 18 to 25

Polybutylphenol (ex 1000 m.w. PIB) (1143g., 0.1 mole) was reacted with glyoxylic acid monohydrate (92g., 1.0 mole) in refluxing xylene (800 c.c.), in the presence of p-toluene sulphonic acid (2.0g.) until no further water was collected in a Dean and Stark water separator. (47 c.c. collected). The solvent was then removed by vacuum-stripping up to a temperature of 170° C.

The resulting intermediate was reacted with a number of different amines by the following general method, details being given in the following Table 3:

The intermediate (118g., 0.1 mole) was stirred with the amine, under nitrogen, at 200° C. in a flask without a condenser, any evolved water being allowed to distil out. The products were diluted with mineral oil to give 85% concentrates and with petroleum spirit (b.p. 62°/68° C), filtered through a filter-aid pad, and the solvent removed by vacuum-stripping up to 180° C.

With the more volatile amines, slightly different techniques were used initially, thus:

a. With dipropylene triamine (Example 19), the reactants were initially heated at 170°-180° C. for ½ hour and at 200° C. for 2 hours under reflux, the condenser being removed for the last 2 hours at 200° C.

b. with ethylenediamine (Example 20) the reactants were heated in refluxing toluene (25 c.c.) for ½ hour, the solvent was distilled out and reaction was continued for 4 hours at 200° C.

c. with dimethylaminopropylamine (Example 22), 100% excess was used, reaction was carried out for 3 hours at 150° C. under reflux, the excess amine was distilled out up to 210° C., and reaction was continued for 4 hours at 200° C.

EXAMPLE 26

Preparation of an amide in oil solution

A mixture of PIB phenol (ex 1300 m.w. PIB) (131.7g., 0.1 mole), glyoxylic acid monohydrate (4.6g., 0.05 mole), p-toluenesulphonic (0.16g.) and mineral oil (25.3g.) was stirred, in an atmosphere of nitrogen for 1½ hours at 140° C. Evolved water was allowed to escape. The mixture was allowed to cool to 80° C., tetraethylenepentamine (9.5g., 0.05 mole) was added and reaction was continued at 200° C. for 4 hours. The product was finally filtered in petroleum spirit solution.

%N: 1.7; (Calc 1.9); TBN: 49 mg. KOH/g.

EXAMPLE 27

Polybutyl phenol (ex 1000 m.w. PIB) (276g., 0.25 mole) was reacted with glyoxylic acid monohydrate (23g., 0.25 mole) in refluxing toluene (150 c.c.) in the presence of p-toluenesulphonic acid (0.4g.) until evolution of water ceased. (12 c.c. collected). Tetraethylenepentamine (47.3g., 0.25 mole) was added, the toluene was distilled out, and reaction at 200° C. was continued for 4 hours to give a polymeric (mono-amide) of tetraethylene pentamine. Nonyl phenol (110g., 0.5 mole) was separately reacted with glyoxylic acid (23g., 0.25 mole) in toluene as above, 12 c.c. of water being collected. The toluene solution was added to the already formed amide, the toluene was distilled out, and reaction again continued for 4 hours at 200° C. Mineral oil (79.8g.) was added, and the product was filtered in petroleum ether solution. Removal of the solvent gave an oil (396g.)

%: N 2.5 (Calc. 3.1); TBN: 64 mg. KOH/g.; TAN: 8 mg. KOH/g.

EXAMPLE 28

A mixture of PIB phenol (ex 1000 m.w. PIB) (243.5g., 0.22 mole) and nonyl phenol (48.4g., 0.22 mole) was reacted with glyoxylic acid (40.5g., 0.44 mole) in refluxing toluene (300 c.c.) until evolution of water ceased. (20 c.c. collected).

Tetraethylenepentamine (41.6g., 0.22 mole) was added, the toluene was distilled out, and reaction was continued at 200° C. for 4 hours. The product was cooled, diluted with mineral oil (61.6g.) and filtered in petroleum ether solution.

Yield: 353g.; %N: 3.6 (Calc. 3.6); TBN: 74 mg. KOH/g.; TAN: 7mg. KOH/g.

EXAMPLE 29

Polypropyl phenol (prepared by alkylation of phenol with 860 m.w. polypropylene using boron trifluoride as catalyst) (100.4g., 0.04 mole) was reacted with glyoxylic acid (3.7g. 0.02 mole), by the method of Example 1.

The resulting intermediate (50.6g., 0.01 mole) was heated with triethylene tetramine (0.73g., 0.005 mole) for 4 hours at 200° C. Mineral oil (9.05g.) was added and the product was filtered in petroleum spirit solution, and finally vacuum-stripped at 180° C.

%N: 0.4 (Calc. 0.5).

EXAMPLE 30

Polybutyl o-cresol, (prepared by boron trifluoride catalysed alkylation of o-cresol with 1000 m.w. polybutene) (66.7g., 0.05 mole) was reacted with glyoxylic acid (2.3g., 0.025 mole) in xylene solution (60 c.c.) using the general method of Example 1.

This intermediate (27.2g., 0.01 mole) was stirred with pentaethylene hexamine (1.16g., 0.005 mole) at 200° C. for 4 hours. Diluent oil (4.95g.) was added and the product filtered in petroleum spirit solution.

%N: 1.0 (Calc. 1.3); TBN: 20 mg. KOH/g.

EXAMPLE 31

To a mixture of polybutyl phenol (ex 1000 m.w. PIB) (194.3g., 0.17 mole), 2-oxoglutaric acid (27.2g., 0.17 mole), petroleum spirit (b.p. 80°-100° C.) (140 c.c.) and water (30 c.c.) was added concentrated sulphuric acid (125 c.c.) with stirring and cooling. The mixture was stirred at room temperature for 6 days, was diluted with further petroleum spirit, and was washed with water/methanol (1:9) (3 × 200 c.c.) Vacuum-stripping to 160° C. gave the acid (148 g.)

Saponification Value: 20.4 mg. KOH/g.

70g. of the above acid were heated with an excess of tetraethylenepentamine (10g.) for 4 hours at 200° C. The mixture was cooled, diluent oil (13g.) and petroleum spirit (300 c.c.) were added, and the solution was washed with water/methanol (1:9). (2 × 40 c.c.). Vacuum-stripping gave the product. (82g.)

%N: 1.0; TBN: 29 mg. KOH/g.

EXAMPLE 32

The product of Example 26 (100.0g., 0.03 mole) was heated with isostearic acid (8.5g., 0.03 mole) for 4 hours at 200° C.

The low residual acidity (5mg. KOH/g.) and the drop of TBN from 49 to 36 KOH/g. showed that the reaction was largely complete. %N: 1.6 (Calc. 1.5).

EXAMPLE 33

A solution of polybutyl phenol (ex 1000 m.w. PIB) (69.3g., 0.07 mole), pyruvic acid (6.2g., 0.07 mole), and p-toluenesulphonic acid (lg.) in xylene was boiled under reflux until water evolution ceased. (3.2 c.c. collected). The solution was filtered and the solvent removed by vacuum-stripping to give the acid intermediate.

23.4g. (0.022 mole) of the intermediate were heated at 200° C. for 4 hours with tetraethylene pentamine (4.17 g. 0.022 mole). Diluent oil (4.76g.) was added and the product was filtered in petroleum ether solution.

%N: 2.3; TBN: 72 mg. KOH/g.

EXAMPLE 34

By a similar method to that of Example 33, polybutyl phenol (ex 1000 m.w. PIB) (114.3g., 0.1 mole) was reacted with pyruvic acid (4.4g., 0.05 mole) in the presence of p-toluenesulphonic acid (0.2g.). The intermediate was not isolated.

Tetraethylene pentamine (4.73g., 0.025 mole) was added, the solvent was distilled out, reaction was continued for 4 hours and the amide was diluted with mineral oil (21.4g) and filtered as normal.

Yield = 128g.; %N = 1.1 (Calc. 1.1); TBN = 31 mg. KOH/g.

EXAMPLE 35

A solution of polyisobutyl phenol (ex 650 m.w. PIB) (87.5g., 0.1 mole), glyoxylic acid monohydrate (4.6g., 0.05 mole) and p-toluenesulphonic acid (0.16g.) in xylene 80 ml.) was heated at reflux temperature until the evolution of water had ceased (1.9 ml. collected).

After allowing to cool, tetraethylene pentamine (4.73g., 0.025 mole) was added, the xylene distilled off and the mixture heated at 200° C. for 4 hours under an atmosphere of nitrogen. The product was diluted with mineral oil (16.6g.) and filtered in petroleum spirit solvent.

Yield = 104g.; %N = 1.8 (Calc. 1.5)

Suitability of the products of the present invention for use as ashless dispersants in lubricants was determined by MS VC and Petter AV-B Engine tests, by Panel Coker Tests and by Spot Tests.

The VC tests were carried out by the standard method on two formulations containing test additives. Formulation A was a 10W/30 blend, formulated to meet U.S. Specification MIL-L46152, containing commercially available metal sulphonate detergents, viscosity index improver and antioxidant/antiwear additive and in which the ashless dispersant normally present (4.5%) was replaced by the test additive, also at 4.5%. The blend had a sulphated ash content of 1%. Formulation B was similar to formulation A, but having a sulphated ash content of 0.5% and containing ashless corrosion inhibitors.

After the tests, merit ratings were assigned according to the condition of the test engine in the usual way and these ratings were as follows:

| Test Additive | Formulation A | | |
|---|---|---|---|
| | Average Sludge (Max 10) | Average Varnish (Max 10) | Piston Skirt Varnish (Max 10) |
| Product of Example 2 | 6.0 | 6.7 | 7.2 |
| Product of Example 6 | 6.7 | 7.2 | 7.4 |
| Product of Example 8 | 8.8 | 8.5 | 8.4 |
| Product of Example 12 | 8.1 | 7.5 | 8.0 |
| Additive X | 4.9 | 7.5 | 7.2 |

| Test Additive | Formulation B | | |
|---|---|---|---|
| | Average Sludge (Max 10) | Average Varnish (Max 10) | Piston Skirt Varnish (Max 10) |
| Product of Example 7 | 7.9 | 8.0 | 8.1 |
| Product of Example 13 | 8.0 | 8.0 | 7.8 |
| Product of repeat of Example 8 (6%) | 9.6 | 9.2 | 9.2 |
| Product of repeat of Example 8 (2.25%) | 5.6 | 8.0 | 7.9 |

All test additives at 4½% concentration except where stated. Additive X is a commercially available ashless dispersant consisting of a borated Mannich base of a polyisobutyl phenol.

The Petter AV-B tests were also carried out according to the standard procedure and merit ratings (maximum 10) assigned in the usual way according to the condition, after test, of various parts of the test engine. Carbon deposition in the grooves of the test engine were also measured. Groove carbon and the overall merit rating (maximum 100) derived from the individual ratings were as follows:

| Test Additive | Groove Carbon (%) | | | Overall Rating |
|---|---|---|---|---|
| | 1st | 2nd | 3rd | |
| Product of Example 3 | 72 | trace | Nil | 81.3 |
| Product of Example 2 | 10 | Nil | Nil | 89.9 |
| Product of Example 5 | 46.3 | Nil | Nil | 79.6 |
| Product of Example 8 | 56.5 | 3.8 | 0.8 | 63.0 |
| Product of Example 12 | 45.5 | 0.8 | Nil | 81.4 |
| Product of Example 14 (2.7%) | 92.0 | 0.6 | Nil | 76.1 |
| Additive X | 93.0 | 30.1 | 0.8 | 50.7 |

The test blend used in the AV-B tests was an SAE 30 blend, formulated to meet the requirements of U.S. Specification MIL-L-2104—C, containing commercially available metal sulphonate detergents, corrosion inhibitor and antioxidant/antiwear additive, and in which the ashless dispersant normally present (3.5%) was replaced by the test additive, also at 3.5% except where stated.

The Panel Coker tests were carried out using the same test blend as for the AV-B test and were carried out for 3½ hours in a slightly modified form of the normal apparatus. Instead of continuous oil splashing, the oil was splashed against the aluminium panel maintained at 600° F. with a cycling procedure consisting of a splashing period of 15 seconds and a 45 second period when the paddle was stationary. The apparatus was further modified to allow a flow of moist air through the sump above the oil surface at the rate of 2.3 liters per hour.

The area of the sump not normally immersed in oil was rated according to the percentage cleanliness in much the same manner as an engine piston is rated after a test such as the Caterpillar 1-G test, to give a % Merit Rating (100 = Perfectly clean). It is believed that the above-mentioned test correlates well with the Caterpillar 1-G Engine Test.

The Merit Ratings obtained were as follows:

| Product of Example No. | Merit Rating |
|---|---|
| 27 | 71.5 |
| 28 | 76.5 |
| 29 | 65.7* |
| 30 | 85.2 |
| 31 | 82.5 |
| 32 | 91.5 |
| 34 | 59.5 |
| 35 | 82.5 |
| Additive X | 61.2 |

*slight sootiness evident.

In the spot tests the test additives were dissolved in mineral oil ($V_{210}$ = 3.5 cS) at 4%. Carbon black (Spheron 9 — ex Cabot Carbon Coy — average particle size — 27 mµ) (1%) was added and the mixtures (10g.) were agitated for 1 hour, using an Ultrasonic Generator in 5 inches × 1 inch test-tubes. The tubes were then stored at 50° C. for 16 hours and allowed to cool. Drops of oil, taken from the top ½inch, were spotted on to chromatography paper, using a fine glass rod. The spots were then allowed to develop for 24 hours, and rated as follows:

| Product of Example No | Dispersancy Rating | Product of Example No | Dispersancy Rating |
|---|---|---|---|
| None - Blank Base Oil | D | 19 | B |
| 5 | A | 20 | B/C |
| 8 | A | 21 | A/B |
| 10 | B | 23 | A |
| 11 | B | 24 | A/B |
| 12 | A/B | 25 | A |
| 13 | A/B | 26 | A/B |
| 15 | A | 28 | A |
| 16 | A | 31 | B |
| 17 | A | 33 | A |
| | | 34 | C/D |
| | | 35 | B |

TABLE 1

| Example No | Phenol/ Acid/ TEPA Ratio | Alkyl Phenol | g (mole) | Glyoxylic[4] Acid g. (mole) | Toluene (c.c.) | TEPA g. (mole) |
|---|---|---|---|---|---|---|
| 3 | 1:1:½ | ex 1000 M.W. PIB | 356 (0.4) | 36.8 (0.4) | 250 | 37.8 (0.2) |
| 4 | 2:1:1 | ex 1000 M.W. PIB | 354.2 (0.32) | 14.7 (0.16) | 300 | 30.2 (0.16) |
| 5 | 1:1:0.75 | ex 1000 M.W. PIB | 296.4 (0.26) | 23.9 (0.26) | 200 | 36.9 (0.195) |
| 6 | 2:1:1 | ex 1000 M.W. PIB | 749.6 (0.78) | 35.9 (0.39) | 600 | 73.7 (0.39) |
| 7 | 2:1:1 | ex 1300 M.W. PIB | 790 (0.6) | 27.6 (0.3) | 200[B] | 56.7 (0.3) |
| 8 | 1:1:1 | ex 2000 M.W. PIB | 1184 (0.5) | 46 (0.5) | 700 | 94.5 (0.5) |
| 9 | 4:3:3 | ex 2000 M.W. PIB | 1134 (0.42) | 29.0 (0.315) | 700[B] | 59.5 (0.315) |
| 10 | 1:1:½ | Thiobis PIB Phenol | 115.8 | 4.6 | 100 | 4.73 |

TABLE 1-continued

| | | | | | | |
|---|---|---|---|---|---|---|
| 11 | 1:1:1 | (ex 1000 M.W. PIB) Methylene-Bis-$^C$ Pib Phenol | (0.05) 49.5 (0.024) | (0.05) 2.2 (0.024) | 50 | (0.025) 2.27 (0.024) |

| Example No | Diluent oil g | % N Found (Calc). | TBN mg. KOH/g. | Panel Coker Test Result |
|---|---|---|---|---|
| 3 | 77 | 2.5 (2.7) | 59 | 78.8 |
| 4 | 68.9 | 1.9 (2.3) | 54 | 66.5 |
| 5 | 60.5 | 2.7 (3.1) | 81 | 71.1 |
| 6 | 148.6 | 2.4 (2.5) | 65 | 61.5 |
| 7 | 151.4 | 1.8 (1.9) | 58 | 59.5 |
| 8 | 229 | 1.85 (2.2) | 51 | 78.5 |
| 9 | 212.7 | 1.3 (1.4) | 36 | 75.5 |
| 10 | 21.6 | 1.0 (1.1) | 21 | 81.2 % S = 1.2 |
| 11 | 9.3 | (1.2) | 27 | |

Note $^A$Monohydrate.
Note $^B$Xylene used as solvent.
Note $^C$Reaction product of PIB phenol and formaldehyde prepared as hereinbefore described.

TABLE 2

| Example No | Phenol/ Acid/ TEPA Ratio | Alkyl Phenol | g (mole) | Glyoxylic$^B$ Acid g (mole) | Toluene (c.c.) | TEPA g. (mole) |
|---|---|---|---|---|---|---|
| 12 | 1:1:1 | ex 1000 M.W. PIB | 664 (0.6) | 55.2 (0.6) | 300 | 113.4 (0.6) |
| 13 | 1:1:1 | ex 1300 M.W. PIB | 579.5 (0.44) | 40.5 (0.44) | 200 | 83.2 (0.44) |
| 14 | 1:1:1 | ex 1000 M.W. PIB | 265.7 (0.24) | 22.1 (0.24) | 150 | 45.4 (0.24) |
| 15 | 1:1:1 | ex 1000 M.W. PIB | 155.0 (0.14) | 12.9 (0.14) | 150 | 26.5 (0.14) |
| 16 | 1:1:1 | ex 1000 M.W. PIB | 287.8 (0.26) | 23.9 (0.26) | 300 | 49.1 (0.26) |
| 17 | 1:1:1 | ex 1000 M.W. PIB | 332.1 (0.3) | 27.6 (0.3) | 350 | 56.7 (0.3) |

| Example No | Other Reactants | g mole | Diluent Oil g. | % N Found (Calc). | TBN mg. KOH/g. | Panel Coker Test Result |
|---|---|---|---|---|---|---|
| 12 | PIBSA ex$^C$ 650 M.W. PIB | 546 (0.6) | 238 | 2.5 (2.5) | 44 | 75$^A$ |
| 13 | PIBSA ex 650 M.W. PIB | 414.9 (0.44) | 193 | 2.05 (2.2) | 34 | 83.7 |
| 14 | Dodecenyl Succinic Anhydride | 64.3 (0.24) | 67.9 | 3.09 (3.5) | 61 | 58.5 |
| 15 | 40% Formalin PIB Phenol (1000 M.W.) | 10.5 (0.14) 155 (0.14) | 60.6 | 2.0 (2.3) | 54 | 77.5 |
| 16 | 40% Formalin Nonyl Phenol | 19.5 (0.26) 58.2 (0.26) | 72 | 2.9 (3.6) | 71 | 68.5 |
| 17 | Benzaldehyde | 31.8 (0.3) | 75.3 | 3.4 (4.0) | 91 | 60.7$^A$ |

Note $^A$Slight sootiness evident.
Note $^B$Monohydrate.
Note $^C$Polyisobutenyl succinic anhydride.

TABLE 3

| Example No | Phenol Glyoxylic Acid/ Amine Ratio | Intermediate g (mole) | AMINE | g (mole) | OIL (g.) |
|---|---|---|---|---|---|
| 18 | 1:1:½ | 118 (0.1) | "Polyamine M" | 9.45 (0.05) | 22.2 |
| 19 | 1:1:½ | 118 (0.1) | Dipropylene Triamine | 6.55 (0.05) | 21.65 |
| 20 | 1:1:1 | 118 (0.1) | Ethylene Diamine | 6 (0.1) | 21.6 |
| 21 | 1:1:½ | 118 (0.1) | Substituted$^A$ Melamine | 11.95 (0.05) | 22.6 |
| 22 | 1:1:1 | 118 (0.1) | Dimethyl- Aminopropylamine | 20.4 (0.2) | 19.0 |
| 23 | 1:1:1 | 118 (0.1) | Bis Amino- Propyl Piperazine | 20.0 (0.1) | 20.6 |

TABLE 3-continued

| | | | | | |
|---|---|---|---|---|---|
| 24 | 1:1:1 | 118 (0.1) | N-(2-Aminoethyl) Ethanolamine | 10.4 (0.1) | 19.0 |
| 25 | 1:1:1 | 118 (0.1) | Bis Hexa- Methylene Triamine | 21.5 (0.1) | 20.7 |

| Example No | YIELD g. | % N (Calc) | TBN mg. KOG/g. | Panel Coker Test Result |
|---|---|---|---|---|
| 18 | 145.8 | 2.2 (2.1) | 47 | 82.7 |
| 19 | 139.2 | 1.3 (1.5) | 16 | — |
| 20 | 140.6 | 1.3 (2.0) | 21 | 60.5 |
| 21 | 149.7 | 2.7 (2.9) | 29 | 83.0 |
| 22 | 145 | 0.7 (1.9) | 14 | |
| 23 | 148 | 3.4 (3.5) | 111 | |
| 24 | 93 | 1.1 (1.9) | 33 | 78 |
| 25 | 151 | 1.9 (2.6) | 54 | 61.3 |

Note ⁴Reaction product of TEPA and Dicyandiamide (intermediate of B.P. 1,068,235).

We claim:

1. A lubricating composition comprising a major amount of a lubricating oil selected from synthetic ester oils, mineral oils and mixtures thereof and containing a minor dispersant amount of an additive having the formula:

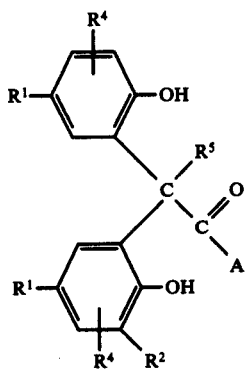

wherein each $R^1$ is the same or different and is a hydrogen atom or an alkyl group, provided that at least one $R^1$ is an alkyl group containing at least 30 up to about 200 atoms; $R^2$ is hydrogen or is a group of the formula:

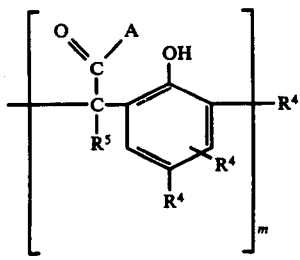

in which $m$ is zero or an integer; each $R^4$ is the same or different and is hydrogen or a group of the formula $-Z-R^6$ in which Z is a sulfur atom, a chain of at least two sulfur atoms or is absent and $R^6$ is an alkyl group, a hydroxy-substituted aralkyl group when Z is absent, a hydroxy-substituted aryl group or a hydroxy-substituted alkaryl group when Z is present; each $R^5$ is the same or different and is a hydrogen atom, a methyl group or the group:

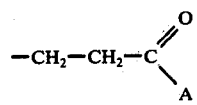

and each

is the same or different and is selected from the group consisting of an amide group or is an ester group wherein said amide group has at least one hydroxyalkyl or aminoalkyl substituent attached to the nitrogen atom and said ester group is derived from an hydroxyethyl substituted amine.

2. A lubricant composition of claim 1 wherein $R^1$ is derived from a poly-alpha-olefin having a molecular weight of 700–3000.

3. A lubricant composition of claim 2 wherein said poly-alpha-olefin is polyisobutylene.

4. A lubricant composition of claim 2 wherein A is derived from an alkylene polyamine containing 1 to about 6 alkyleneamine units.

5. A lubricant composition of claim 4 wherein said alkylene polyamine is an ethylene polyamine containing from 1 to about 6 ethyleneamine units.

6. A lubricant composition of claim 1 wherein $R^5$ is hydrogen.

7. A lubricant composition of claim 6 wherein $R^1$ is derived from poly-alpha-olefin having a molecular weight of about 700–3000.

8. A lubricant composition of claim 7 wherein A is derived from an alkylene polyamine containing from 1 to about 6 alkyleneamine units.

9. A lubricant composition of claim 8 wherein said alkylene polyamine is an ethylene polyamine containing from 1 to about 6 ethyleneamine units.

10. A lubricant composition of claim 9 wherein $R^1$ is derived from polyisobutylene.

* * * * *